United States Patent
Karl

(12) 
(10) Patent No.: US 8,613,963 B2
(45) Date of Patent: Dec. 24, 2013

(54) NUTRITIONAL SUPPLEMENT

(75) Inventor: Mitchell Karl, Boca Raton, FL (US)

(73) Assignee: Healthy Drink Discoveries Incorporated, Boca Raton, FL (US)

( * ) Notice: Subject to any disclaimer, the term of this patent is extended or adjusted under 35 U.S.C. 154(b) by 219 days.

(21) Appl. No.: 12/861,898

(22) Filed: Aug. 24, 2010

(65) Prior Publication Data

US 2010/0316758 A1 Dec. 16, 2010

Related U.S. Application Data

(63) Continuation-in-part of application No. 12/576,035, filed on Oct. 8, 2009, now abandoned, which is a continuation-in-part of application No. 12/120,765, filed on May 15, 2008, now abandoned.

(60) Provisional application No. 60/942,122, filed on Jun. 5, 2007.

(51) Int. Cl.
*A23K 1/18* (2006.01)
(52) U.S. Cl.
USPC .......... 426/2; 426/72; 426/419; 426/531; 426/590; 426/656; 426/658; 514/7.4
(58) Field of Classification Search
None
See application file for complete search history.

(56) References Cited

U.S. PATENT DOCUMENTS

| 6,068,705 A * | 5/2000 | Tang et al. ............. 127/32 |
| 6,365,176 B1 * | 4/2002 | Bell et al. ............. 424/439 |
| 2006/0003947 A1 * | 1/2006 | Udell ............. 514/26 |

OTHER PUBLICATIONS

Seki et al., Asia Pac J Clin Nutr., 2003, vol. 12, No. 3, p. 282-91, Abstract Only.*

* cited by examiner

*Primary Examiner* — Kade Ariani
(74) *Attorney, Agent, or Firm* — Johnson & Martin, P.A.; James David Johnson

(57) ABSTRACT

A nutritional supplement specifically designed to lower cholesterol that addresses multiple mechanisms including hepatic synthesis and release, intestinal absorption of cholesterol, while, at the same time, including ingredients that mitigate the side effects of the constituents and increase their efficacy by affecting emotional factors that influence compliance such as a sense of well-being and euphoria on the one hand, or an increased overall metabolism and desire for the product stemming from its coloration on the other hand. The nutritional supplement can be prepared as a powder that can be added to a food item by a human subject, a concentrate that can be mixed with water or another beverage, or incorporated into a baked good for ingestion by the human subject.

6 Claims, No Drawings

US 8,613,963 B2

NUTRITIONAL SUPPLEMENT

CROSS-REFERENCE TO RELATED APPLICATION

This application is a continuation-in-part of U.S. nonprovisional patent application Ser. No. 12/576,035 filed on Oct. 8, 2009, which is a continuation-in-part application of U.S. nonprovisional patent application Ser. No. 12/120,765 filed on May 15, 2008, which claims the priority of U.S. provisional patent application Ser. No. 60/942,122 filed on Jun. 5, 2007.

FIELD OF THE INVENTION

This invention relates to nutritional supplements. More particularly, the invention relates to compositions and methods for supplementing the diet for improving health and preventing disease.

BACKGROUND

Chronically elevated blood levels of cholesterol lead to cardiovascular disease as the cholesterol finds its way into the walls of blood vessels and damages them. This ultimately results in symptoms of chronic arterial insufficiency such as angina and claudication on the one hand, and acute vascular insufficiency, such as heart attack and stroke on the other.

Over $120 billion dollars is spent on direct and indirect costs associated with cardiovascular disease annually in the United States alone. Cardiovascular disease incidence increases with serum LDL cholesterol in a log linear fashion and more importantly declines with treatment-induced reduction of serum LDL cholesterol.

Conventional therapy for elevated blood cholesterol levels takes the form of four classes of FDA approved medications: statins, bioresins, fibrates, and niacin.

Of these, statins are the most widely used with greater than $20 billion in annual sales; however, all the classes, including statins, have side effects and at higher doses, that are necessary to achieve targets, result in side effects that limit their utility. This is especially so of niacin and statins.

Recently, it has been appreciated that in attempting to lower cholesterol, two or more drugs with different mechanisms of action can lower toxicity and produce synergy in the cholesterol lowering effect. Vytorin, a recently introduced combination of Zetia and Simvastatin, has been shown to decrease cholesterol absorption and synthesis and reduce cholesterol better than the sum of the expected reduction of either drug alone. This is explained by a phenomenon I refer to as "escape homeostasis." When one pathway to cholesterol elevation is blocked, an alternative pathway is often enhanced by the body, so that the overall cholesterol levels are maintained. There is, thus, a built-in or automatic drug resistance that can only be overcome with multiple active agents working simultaneous at different sites. It is noteworthy that evidence exists that even homeopathic, previously felt sub-therapeutic amounts of biologically active cholesterol lowering compounds can exert powerful efficacy with minimal side effects when combined with other agents that work by alternative pathways.

SUMMARY

The invention is based on the development of a cholesterol lowering nutritional supplement that utilizes multiple mechanisms and sites of action to reduce cholesterol and also has ingredients that reduce toxicity, increase the rate of metabolism both on a general and a cellular level and, finally stimulate compliance by causing a sense of mild euphoria and well-being, as well as enhancing metabolism.

Accordingly, in one aspect, the invention features a nutritional supplement that includes at least two active ingredients selected from among the following: niacin, a phytosterol component, red yeast rice, coenzyme Q10, L-carnitine, and ascorbic acid.

In another aspect, the invention can feature the nutritional supplement further including water, juice, or juice concentrate.

In another aspect, the invention can feature the nutritional supplement prepared as a baked good, a concentrate, or a powder.

In another aspect, the invention can feature each serving of the nutritional supplement including about 5 to 100 mg of niacin.

In another aspect, the invention can feature each serving of the nutritional supplement including about 400 to 3,000 mg of the phytosterol component.

In another aspect, the invention can feature each serving of the nutritional supplement including about 300 to 3,000 mg of red yeast rice.

In another aspect, the invention can feature each serving of the nutritional supplement including about 50 to 250 mg of L-carnitine.

In another aspect, the invention can feature each serving of the nutritional supplement including about 300 to 1,200 mg of ascorbic acid.

In another aspect, the invention can feature each serving of the nutritional supplement including about 10 to 200 mg of coenzyme Q10.

In another aspect, the invention can feature each serving of the nutritional supplement including less than about 50 mg of niacin.

In another aspect, the invention can feature the phytosterol component including at least one phytosterol ester.

In another aspect, the invention can feature the nutritional supplement including at least three active ingredients selected from among the following: niacin, a phytosterol component, red yeast rice, coenzyme Q10, L-carnitine, and ascorbic acid.

In another aspect, the invention can feature the nutritional supplement including at least four active ingredients selected from among the following: niacin, a phytosterol component, red yeast rice, coenzyme Q10, L-carnitine, and ascorbic acid.

In another aspect, the invention can feature the nutritional supplement including at least five active ingredients selected from among the following: niacin, a phytosterol component, red yeast rice, coenzyme Q10, L-carnitine, and ascorbic acid.

In another aspect, the invention can feature the nutritional supplement including niacin, a phytosterol component, red yeast rice, coenzyme Q10, L-carnitine, and ascorbic acid.

In another aspect, the invention features the nutritional supplement including maltodextrin.

In another aspect, the invention can feature the nutritional supplement including two daily servings. Each serving can include as ingredients water or juice, about 5 to 50 mg of niacin, about 500 to 1,500 mg of at least one phytosterol ester, about 300 to 1,500 mg of red yeast rice, about 10 to 200 mg of coenzyme Q10, about 50 to 250 mg of L-carnitine, and about 300 to 1,200 mg of ascorbic acid.

In another aspect, the invention can feature two servings of the nutritional supplement being packaged in a container.

The invention also features a method that includes the step of administering to a subject for at least 7 days a nutritional supplement comprising at least two active ingredients selected from among the following: niacin, a phytosterol component, red yeast rice, coenzyme Q10, L-carnitine, and ascorbic acid.

In another aspect, the method can also feature the step of administering the nutritional supplement to the subject twice daily.

In another aspect, the method can also feature the step of preparing the nutritional supplement in a form selected from among a baked good, a concentrate, or a powder.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control.

DETAILED DESCRIPTION

The invention provides an aqueous composition of ingredients and dietary supplements to yield a cholesterol lowering drink. The composition is typically contained within a two-serving container such as a can or bottle and includes water and a combination of at least two of niacin, a phytosterol component, red yeast rice, coenzyme Q10, L-carnitine, and ascorbic acid in amount effective to reduce serum cholesterol levels in a subject who drinks the composition on a regular basis (e.g., once a day, twice a day, every two days, or every three days).

The active ingredients are preferably included at a concentration effective to reduce a subject's serum cholesterol by at least 10% (e.g., at least 20, 30, 40, or 50%) when included in combination with each other and administered to the subject on a regular basis (e.g., twice a day or once a day for at least 2, 3, 4, 5, 6, 12, or 24 weeks). In an exemplary embodiment, the composition can be administered twice daily to the subject in the form of and as part of a beverage, e.g., as a nutritional drink.

Niacin lowers cholesterol by inhibiting lipoprotein formation or release in the liver. Phytosterols lower cholesterol by competing for absorption in the intestines. Red Yeast Rice is a dietary supplement and coloring agent that has been used in Chinese food and medicines for centuries. It decreases synthesis and absorption of cholesterol, produces red coloration which stimulates appetite, compliance, and metabolism. On a cellular level, L-carnitine and coenzyme Q10 enhance transport of fatty acids to the mitochondria and enhance the burning of fatty acids respectively. L-carnitine can also cause a mild sense of euphoria, a beneficial effect that may result in greater compliances with the preparation containing it. Ascorbic acid changes the constitution of bile to decrease cholesterol absorption and inhibit the HMG-CoA reductase pathway, the rate-limiting step in cholesterol biosynthesis.

In an exemplary embodiment, the phytosterol component can include one or more phytosterol esters.

In one embodiment, the beverage can include 6.9 g of a composition in a 8-ounce container. The beverage can be packaged in a bottle or other container that contains two servings, e.g., two 4-ounce servings in an 8-ounce container. The composition can include the following ingredients in each 4-ounce serving: about 12.5 mg of niacin (niacinamide), about 500 mg of vitamin C (ascorbic acid), about 150 mg of L-carnitine (L-carnitine-L-tartrate), about 25 mg of coenzyme Q10, about 660 mg of phytosterol esters, and q.s. maltodextrin. Servings of the beverage can be consumed twice daily, for example, one serving in the morning and one serving at night.

In another embodiment, the beverage can include 8.2 g of a composition in an 8-ounce container. The beverage can be packaged in a bottle or other container that contains two servings, e.g., two 4-ounce servings in an 8-ounce container. The composition can include the following ingredients in each 4-ounce serving: about 600 mg of red yeast rice powder, about 12.5 mg of niacin (niacinamide), about 500 mg of vitamin C (ascorbic acid), about 150 mg of L-carnitine (L-carnitine-L-tartrate), about 25 mg of coenzyme Q10, about 660 mg of phytosterol esters, and q.s. maltodextrin. Servings of the beverage can be consumed twice daily, for example, one serving in the morning and one serving at night.

Although 4-ounce servings and 8-ounce containers are described herein, the serving size and container size can be different as long as the amounts of each ingredient remain consistent. For example, each serving can be 3.5, 4.5, 5, 6, 7, 7.5, 8.5, 9, 10, 12, 13, 14, or 16 ounces.

Each serving of the composition can include niacin in the amounts of about 4.5, 5, 6, 6.1, 6.5, 6.6, 6.9, 7, 7.5, 8, 9, 9.9, 10, 10.1, 10.5, 11, 11.5, 11.9, 12, 12.1, 12.5, 12.6, 12.9, 13, 15, 19, 20, 25, 30, 40, 50, 60, 70, 75, 80, 90, 99, 100, 101, or 110 mg or more. In exemplary embodiments, each serving of the composition can contain less than about 50 mg of niacin. In one exemplary embodiment, each serving of the composition can contain about 12.5 mg of niacin.

Each serving of the composition can include phytosterol esters in the amounts of about 300, 400, 500, 550, 600, 625, 640, 649, 651, 660, 675, 700, 800, 900, 1,000, 1,250, 1,320, 1,500, 1,800, 1,900, 1,950, 1,999, 2,000, 2,001, 2,050, or 2,100 mg or more. In exemplary embodiments, each serving of the composition can contain about 660 mg of phytosterol esters.

Each serving of the composition can include coenzyme Q in the amounts of about 8, 9, 10, 13, 15, 17, 19, 20, 22.5, 24, 24.5, 24.9, 25, 25.1, 25.5, 26, 27, 27.5, 28, 29, 30, 35, 40, 45, 50, 55, 75, 90, 100, 150, 200, 250, or 300 mg or more. In exemplary embodiments, each serving of the composition can contain about 25 mg of coenzyme Q.

Each serving of the composition can include L-carnitine in the amounts of about 90, 95, 100, 110, 115, 125, 135, 140, 145, 149, 149.1, 149.9, 150, 150.1, 150.5, 151, 153, 155, 160, 170, 175, 180, 190, 200, 250, 300, 400, or 500 mg or more. In exemplary embodiments, each serving of the composition can contain about 75-150 mg of L-carnitine. In one exemplary embodiment, each serving of the composition can contain about 150 mg of L-carnitine.

Each serving of the composition can include ascorbic acid in the amounts of about 50, 100, 200, 250, 300, 400, 450, 475, 490, 499, 499.1, 500, 500.1, 500.5, 501, 510, 520, 535, 550, 600, 625, 640, 649, 651, 660, 675, 700, 800, 900, 1,000, 1,500, or 2,000 mg or more. In exemplary embodiments, each serving of the composition can contain about 500 mg of ascorbic acid.

Each serving of the composition can include red yeast rice in the amounts of about 300, 400, 500, 550, 575, 590, 595, 599, 599.1, 599.9, 600, 600.1, 600.5, 601, 610, 620, 625, 640, 650, 660, 675, 700, 800, 900, 1,000, 1,250, 1,500, 1,800, 1,900, 1,950, 1,999, 2,000, 2,001, 2,050, 2,100, or 2,400 mg or more. In exemplary embodiments, each serving of the composition can contain about 600 mg of red yeast rice.

The composition can also feature maltodextrin making up the remainder of any 6.9 g, 8.2 g, or other amount of the composition premixture before the addition of water to create the beverage. The beverage may also contain artificial or natural flavorings and colorings.

EXAMPLE 1

A beverage for administration twice daily to a human subject can include two servings stored in a container such as, for example, a bottle. Each serving of the beverage can include water (100-500 ml) and 6.9 g of the composition. The composition can include as ingredients phytosterol esters (about 660 mg), niacin (less than about 50 mg), coenzyme Q10 (about 25 mg), ascorbic acid (about 500 mg), L-carnitine (about 75-150 mg), and maltodextrin (q.s.).

EXAMPLE 2

A beverage for administration twice daily can include two servings stored in a container such as, for example, a bottle or can. Each serving of the beverage can include water (about 100 to 500 ml) and 8.2 g of the composition. As ingredients, the composition can feature phytosterol esters (about 660 mg), niacin (less than about 50 mg), red yeast rice (about 600 mg), coenzyme Q10 (about 25 mg), ascorbic acid (about 500 mg), L-carnitine (about 75-150 mg), and maltodextrin (q.s.).

In an exemplary method of the invention, the composition can be administered to a human subject at least twice daily in the form of a beverage or nutritional drink. The two daily doses of the beverage can be contained within a single container such as, for example, a bottle or can. In another embodiment, each serving of the beverage can be packaged in a separate bottle or container. The beverage can be administered twice daily for at least 7 days. The beverage can include water and at least two active ingredients selected from among the following: niacin, a phytosterol component, red yeast rice, coenzyme Q10, L-carnitine, and ascorbic acid.

In another method of the invention, the composition may be administered at an interval different than twice daily, e.g., once, three times, or four times daily.

In still another method of the invention, the composition can be administered to a human subject to reduce the subject's blood cholesterol levels.

The invention can also include a nutritional supplement that can be created as a powder that can be added to food items, as a baked good (e.g., as cookies and brownies), and as a concentrate. The concentrate can be added to water or another ingestible liquid to create a nutritional beverage. Thus, the nutritional supplement can be provided in an ingestible form that can lower cholesterol in human subjects. The nutritional supplement is typically contained within a two-serving container such as a package, box, carton, wrapper, bottle or can. Where the nutritional supplement is prepared in the form of a concentrate that can be added to and mixed with a beverage, a bottle or can be used for packaging the concentrate. The nutritional supplement can include a combination of at least two of niacin, a phytosterol component, red yeast rice, coenzyme Q10, L-carnitine, and ascorbic acid in amounts effective to reduce serum cholesterol levels in a subject who ingest the composition on a regular basis (e.g., once a day, twice a day, every two days, or every three days). The nutritional supplement can also include water.

As with the nutritional beverage, the active ingredients of the nutritional supplement are preferably included at a concentration effective to reduce a subject's serum cholesterol by at least 10% (e.g., at least 20, 30, 40, or 50%) when included in combination with each other and administered to the subject on a regular basis (e.g., twice a day or once a day for at least 2, 3, 4, 5, 6, 12, or 24 weeks). In an exemplary embodiment, the composition can be administered twice daily to the subject in the form of and as part of a powder that can be added to food items, incorporated into a baked good (e.g., as a snack bar, a cookie or a brownie), or as a concentrate mixed with water or another beverage.

In an exemplary embodiment, the phytosterol component can include one or more phyto sterol esters.

In one embodiment, the nutritional supplement can include 6.9 g of a composition in an 8-ounce container. The nutritional supplement can be packaged in a container that contains two servings, e.g., two 4-ounce servings in an 8-ounce container. The composition of this embodiment of the nutritional supplement can include the following ingredients in each 4-ounce serving: about 12.5 mg of niacin (niacinamide), about 500 mg of vitamin C (ascorbic acid), about 150 mg of L-carnitine (L-carnitine-L-tartrate), about 25 mg of coenzyme Q10, about 660 mg of phytosterol esters, and q.s. maltodextrin. Servings of the nutritional supplement can be consumed twice daily, for example, one serving in the morning and one serving at night.

In another embodiment, the nutritional supplement can include 8.2 g of a composition in an 8-ounce container. The beverage can be packaged in a bottle or other container that contains two servings, e.g., two 4-ounce servings in an 8-ounce container. The composition of this embodiment of the nutritional supplement can include the following ingredients in each 4-ounce serving: about 600 mg of red yeast rice powder, about 12.5 mg of niacin (niacinamide), about 500 mg of vitamin C (ascorbic acid), about 150 mg of L-carnitine (L-carnitine-L-tartrate), about 25 mg of coenzyme Q10, about 660 mg of phytosterol esters, and q.s. maltodextrin. Servings of the nutritional supplement can be consumed twice daily, for example, one serving in the morning and one serving at night.

Although 4-ounce servings and 8-ounce containers are described herein, the serving size and container size can be different as long as the amounts of each ingredient remain consistent. For example, each serving can be 3.5, 4.5, 5, 6, 7, 7.5, 8.5, 9, 10, 12, 13, 14, or 16 ounces.

Each serving of the nutritional supplement can include niacin in the amounts of about 4.5, 5, 6, 6.1, 6.5, 6.6, 6.9, 7, 7.5, 8, 9, 9.9, 10, 10.1, 10.5, 11, 11.5, 11.9, 12, 12.1, 12.5, 12.6, 12.9, 13, 15, 19, 20, 25, 30, 40, 50, 60, 70, 75, 80, 90, 99, 100, 101, or 110 mg or more. In exemplary embodiments, each serving of the nutritional supplement can contain less than about 50 mg of niacin. In one exemplary embodiment, each serving of the nutritional supplement can contain about 12.5 mg of niacin.

Each serving of the nutritional supplement can include phytosterol esters in the amounts of about 300, 400, 500, 550, 600, 625, 640, 649, 651, 660, 675, 700, 800, 900, 1,000, 1,250, 1,320, 1,500, 1,800, 1,900, 1,950, 1,999, 2,000, 2,001, 2,050, or 2,100 mg or more. In exemplary embodiments, each serving of the nutritional supplement can contain about 660 mg of phytosterol esters.

Each serving of the nutritional supplement can include coenzyme Q in the amounts of about 8, 9, 10, 13, 15, 17, 19, 20, 22.5, 24, 24.5, 24.9, 25, 25.1, 25.5, 26, 27, 27.5, 28, 29, 30, 35, 40, 45, 50, 55, 75, 90, 100, 150, 200, 250, or 300 mg or more. In exemplary embodiments, each serving of the nutritional supplement can contain about 25 mg of coenzyme Q.

Each serving of the nutritional supplement can include L-carnitine in the amounts of about 90, 95, 100, 110, 115, 125, 135, 140, 145, 149, 149.1, 149.9, 150, 150.1, 150.5, 151, 153, 155, 160, 170, 175, 180, 190, 200, 250, 300, 400, or 500 mg or more. In exemplary embodiments, each serving of the nutritional supplement can contain about 75-150 mg of L-carnitine. In one exemplary embodiment, each serving of the nutritional supplement can contain about 150 mg of L-carnitine.

Each serving of the nutritional supplement can include ascorbic acid in the amounts of about 50, 100, 200, 250, 300, 400, 450, 475, 490, 499, 499.1, 500, 500.1, 500.5, 501, 510, 520, 535, 550, 600, 625, 640, 649, 651, 660, 675, 700, 800, 900, 1,000, 1,500, or 2,000 mg or more. In exemplary embodiments, each serving of the nutritional supplement can contain about 500 mg of ascorbic acid.

Each serving of the nutritional supplement can include red yeast rice in the amounts of about 300, 400, 500, 550, 575, 590, 595, 599, 599.1, 599.9, 600, 600.1, 600.5, 601, 610, 620, 625, 640, 650, 660, 675, 700, 800, 900, 1,000, 1,250, 1,500, 1,800, 1,900, 1,950, 1,999, 2,000, 2,001, 2,050, 2,100, or 2,400 mg or more. In exemplary embodiments, each serving of the nutritional supplement can contain about 600 mg of red yeast rice.

The nutritional supplement can also feature maltodextrin making up the remainder of any 6.9 g, 8.2 g, or other amount of the nutritional supplement premixture before the addition of water or other food ingredients. The nutritional supplement may also contain artificial or natural flavorings and colorings.

The invention can also include a method in which the composition can be administered to a human subject at least twice daily in the form of a nutritional supplement. The nutritional supplement can be created as a solid such as, for example, a powder that can be added to food items or as a baked good (e.g., as cookies and brownies). The method can also include the nutritional supplement being a concentrate that can be added to water or another ingestible liquid to create a nutritional beverage. The two daily doses of the nutritional supplement can be contained within a single container such as, for example, a package, box, carton, wrapper, bottle or can. In another embodiment, each serving of the nutritional supplement can be packaged in a separate bottle or container. The nutritional supplement can be administered twice daily for at least 7 days. The nutritional supplement can include at least two active ingredients selected from among the following: niacin, a phytosterol component, red yeast rice, coenzyme Q10, L-carnitine, and ascorbic acid.

In another method of the invention, the nutritional supplement composition may be administered at an interval different than twice daily, e.g., once, three times, or four times daily. For example, the nutritional supplement can be ingested by the human subject in the form of a cookie, brownie, or snack bar. In another example, the nutritional supplement can be provided in the form of a powder, which can be mixed in or sprinkled onto other food items and ingested by the human subject. In still another example, the nutritional supplement can be provided in the form of a concentrate that can be mixed with a beverage selected by the human subject and then imbibed by the human subject.

In still another method of the invention, the composition can be administered to a human subject in the nutritional supplement to reduce the subject's blood cholesterol levels.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A cholesterol-lowering nutritional supplement comprising niacin, a phytosterol component comprising at least one phytosterol ester, red yeast rice, coenzyme Q10, L-carnitine, maltodextrin, and ascorbic acid;
   wherein the nutritional supplement comprises two daily servings, each serving comprising water or juice, about 5 to 50 mg of niacin, about 600 to 1,500 mg of at least one phytosterol ester, about 300 to 1,500 mg of red yeast rice, about 10 to 200 mg of coenzyme Q10, about 50 to 150 mg of L-carnitine, and about 450 to 1,200 mg of ascorbic acid.

2. The nutritional supplement of claim 1, wherein the nutritional supplement further comprises water, juice, or juice concentrate.

3. The nutritional supplement of claim 1, wherein the nutritional supplement is produced in a form selected from the group consisting of: a baked good, a concentrate, and a powder.

4. A method for lowering cholesterol comprising the step of administering to a subject for at least 7 days a nutritional supplement, the nutritional supplement comprising niacin, a phytosterol component comprising at least one phytosterol ester, red yeast rice, coenzyme Q10, L-carnitine, maltodextrin, and ascorbic acid;
   wherein the nutritional supplement comprises two daily servings, each serving comprising water or juice, about 5 to 50 mg of niacin, about 600 to 1,500 mg of at least one phytosterol ester, about 300 to 1,500 mg of red yeast rice, about 10 to 200 mg of coenzyme Q10, about 50 to 150 mg of L-carnitine, and about 450 to 1,200 mg of ascorbic acid.

5. The method of claim 4, wherein the nutritional supplement is administered to the subject twice daily.

6. The method of claim 4, wherein the method further comprises the step of preparing the nutritional supplement in a form selected from the group consisting of: a baked good, a concentrate, and a powder.

* * * * *